(12) United States Patent
Zhao et al.

(10) Patent No.: US 11,878,078 B2
(45) Date of Patent: *Jan. 23, 2024

(54) INSTANT RELEASE PHARMACEUTICAL PREPARATION OF ANTICOAGULANT AND PREPARATION METHOD THEREFOR

(71) Applicant: Jiangsu Vcare PharmaTech Co., Ltd., Nanjing (CN)

(72) Inventors: Yanlei Zhao, Nanjing (CN); Jianjun Zhang, Nanjing (CN); Xuefang Liu, Nanjing (CN); Yuan Gao, Nanjing (CN); Hongbin Sun, Nanjing (CN); Yanchun Gong, Nanjing (CN); Yongqiang Liu, Nanjing (CN)

(73) Assignee: Jiangsu Vcare PharmaTech Co., Ltd., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/969,972

(22) Filed: Oct. 20, 2022

(65) Prior Publication Data
US 2023/0124923 A1 Apr. 20, 2023

Related U.S. Application Data

(63) Continuation of application No. 16/975,329, filed as application No. PCT/CN2018/083208 on Apr. 16, 2018, now Pat. No. 11,478,432.

(51) Int. Cl.
| | | |
|---|---|---|
| *A61K 9/48* | (2006.01) | |
| *A61K 9/00* | (2006.01) | |
| *A61K 9/20* | (2006.01) | |
| *A61K 9/28* | (2006.01) | |
| *A61K 31/4365* | (2006.01) | |

(52) U.S. Cl.
CPC .......... *A61K 9/4808* (2013.01); *A61K 9/0053* (2013.01); *A61K 9/2009* (2013.01); *A61K 9/2013* (2013.01); *A61K 9/2027* (2013.01); *A61K 9/2054* (2013.01); *A61K 9/2059* (2013.01); *A61K 9/2095* (2013.01); *A61K 9/28* (2013.01); *A61K 9/485* (2013.01); *A61K 9/4833* (2013.01); *A61K 9/4858* (2013.01); *A61K 9/4866* (2013.01); *A61K 31/4365* (2013.01)

(58) Field of Classification Search
CPC .. A61K 9/4808; A61K 9/0053; A61K 9/2009; A61K 9/2013; A61K 9/2027; A61K 9/2054; A61K 9/2059; A61K 9/2095; A61K 9/28; A61K 9/4833; A61K 9/485; A61K 9/4858; A61K 9/4866; A61K 31/4365
See application file for complete search history.

(56) References Cited

U.S. PATENT DOCUMENTS

| | | |
|---|---|---|
| 2013/0011473 A1 | 1/2013 | Lei et al. |
| 2014/0154330 A1 | 6/2014 | Cho et al. |
| 2020/0397709 A1 | 12/2020 | Zhao et al. |

FOREIGN PATENT DOCUMENTS

| | | |
|---|---|---|
| CN | 102863457 A | 1/2013 |
| CN | 103720700 A | 4/2014 |
| CN | 103772270 A | 5/2014 |
| CN | 104644595 A | 5/2015 |
| CN | 105168166 A | 12/2015 |
| CN | 108420798 A | 8/2018 |
| JP | 2011-520978 A | 7/2011 |
| JP | 2016-530331 A | 9/2016 |
| JP | 2017-511331 A | 4/2017 |
| WO | 2009/143297 A1 | 11/2009 |
| WO | 2014/056418 A1 | 4/2014 |
| WO | 2015/038993 A1 | 3/2015 |
| WO | 2015/153613 A1 | 10/2015 |

OTHER PUBLICATIONS

Horiba Scientific, A Guidebook to Particle Size Analysis, Why is particle size important? Horiba Instruments, Inc., 34 pages, (2017).
Rasenack et al., Micron-size drug particles: common and novel micronization techniques. Pharm Dev Technol. 2004;9(1):1-13.
International Search Report and Written Opinion for Application No. PCT/CN2018/083208, dated Jan. 18, 2019, 8 pages.

*Primary Examiner* — Robert A Wax
*Assistant Examiner* — Olga V. Tcherkasskaya
(74) *Attorney, Agent, or Firm* — McCarter & English, LLP; Wei Song; Peng Cai

(57) ABSTRACT

The present invention relates to the technical field of medicine and relates to an instant release pharmaceutical preparation of an anticoagulant and a preparation method therefor. The instant release pharmaceutical preparation of an anticoagulant comprises a vicagrel compound or a pharmaceutically acceptable form thereof, the preparation is a tablet or a capsule, the vicagrel or the pharmaceutically acceptable form thereof is provided at a suitable particle size, and the D90 thereof <50 μm. With regard to the drug-containing particles obtained by the present invention, a pharmaceutical preparation formed therefrom exhibits rapid release characteristics in an in vitro dissolution test and exhibits considerable advantages in pharmacokinetics in vivo, showing a greater degree (AUC) and rate ($C_{max}$) of drug absorption. Further provided by the present invention is a method for preparing an instant release pharmaceutical preparation of an anticoagulant; according to the formulation of the drug-containing particles as disclosed by the present invention, a capsule or tablet instant release preparation having excellent stability may be obtained by means of a combination of optional preparation steps.

6 Claims, 2 Drawing Sheets

INSTANT RELEASE PHARMACEUTICAL PREPARATION OF ANTICOAGULANT AND PREPARATION METHOD THEREFOR

RELATED APPLICATIONS

This application is a Continuation of U.S. application Ser. No. 16/975,329, filed on Aug. 24, 2020, which is the U.S. national stage filing, under 35 U.S.C. § 371(c), of International Application No. PCT/CN2018/083208, filed on Apr. 16, 2018. The entire contents of the aforementioned applications are incorporated herein by reference in their entirety.

FIELD OF THE INVENTION

The present invention relates to the technical field of medicine, and provides an instant release pharmaceutical preparation, specifically including an instant release tablet or capsule comprising an anticoagulant vicagrel and an acceptable salt carrier thereof. The present invention also provides a method for preparing the instant release pharmaceutical preparation.

BACKGROUND OF THE INVENTION

Vicagrel, as a novel antiplatelet aggregation drug, can be used to overcome the clinical application defects of existing antiplatelet drugs, such as "clopidogrel resistance" and high risk of bleeding with prasugrel. Vicagrel has entered the stage of clinical research and is expected to be developed into a safer and more effective novel antiplatelet drug.

Patent CN103254211B has disclosed a method for preparing vicagrel and derivatives thereof. Patent CN103720700A has disclosed a composition of vicagrel and aspirin for use in prevention or treatment of diseases caused by thrombosis. However, at present, there is no report on the formulation process of a preparation with vicagrel as a single active ingredient. As an anticoagulant drug, it is required to quickly reach an effective blood drug concentration in vivo to exert its therapeutic effect, and the development of an oral instant release preparation is particularly necessary.

SUMMARY OF THE INVENTION

An objective of the present invention is to provide an instant release preparation of vicagrel. In view of this, the present invention designs an oral pharmaceutical preparation for instant release that may be a capsule or tablet or granule, which comprises vicagrel or a pharmaceutically acceptable form thereof.

The technical solution adopted by the present invention is as follows.

An instant release pharmaceutical preparation of an anticoagulant comprises a vicagrel compound or a pharmaceutically acceptable form thereof, wherein the preparation is a tablet or a capsule, the vicagrel or the pharmaceutically acceptable salt thereof is provided at a suitable particle size, and the diameter of 90% of the particles (D90) thereof is <50 μm.

The pharmaceutically acceptable form of vicagrel described in the present invention includes, but is not limited to, a salt, a solvate and other pharmaceutically acceptable carriers of vicagrel, which have the pharmaceutical activity of vicagrel.

With regard to the instant release preparation provided by the present invention, the bulk drug is pulverized, and the particle size thereof is preferably D90<50 μm, further preferably D90<30 μm, and most preferably D90<15 μm.

In one embodiment of the present invention, the instant release pharmaceutical preparation is in the form of drug-containing particles for filling into a capsule or forming a tablet, which comprise:
- a) an active ingredient of vicagrel: vicagrel or a pharmaceutically acceptable form thereof;
- b) one or more fillers;
- c) one or more disintegrants;
- d) one or more binders; and
- e) one or more glidants/lubricants.

Preferably, the proportions of the components are as follows:
- a) the active ingredient of vicagrel comprising 0.5%-30% wt of a tablet or capsule filling;
- b) the fillers in the range of 1%-95% wt of the tablet or capsule filling;
- c) the binders in the range of 0%-20% wt of the tablet or capsule filling;
- d) the disintegrants in the range of 0%-20% wt of the tablet or capsule filling;
- e) the glidants/lubricants in the range of 0%-5% wt of the tablet or capsule filling; and
- f) the stabilizers in the range of 0%-5% wt;

the sum of the percentages of all components being 100%.

In one embodiment, the drug-containing particles comprise vicagrel and one or more fillers. Suitable fillers include, for example, microcrystalline cellulose, lactose, pregelatinized starch/starch, mannitol, or other commonly used fillers known in the art, or a combination thereof. In other embodiments, the drug-containing particles optionally comprise one or more of the following adjuvants: (1) one or more binders; (2) one or more disintegrants; and (3) one or more glidants/lubricants. Suitable binders include, for example, hydroxypropyl methylcellulose, hydroxypropyl cellulose, polyvinylpyrrolidone, and others known in the art. Suitable disintegrants include, for example, low-substituted hydroxypropyl cellulose, croscarmellose sodium, sodium carboxymethyl starch, crospovidone, and others known in the art. Suitable glidants/lubricants include, for example, silica, magnesium stearate, sodium stearyl fumarate, and others known in the art.

When the drug-containing particles are filled in capsules or compressed into tablets, vicagrel is present in the form of 1-30 mg per unit preparation, and the daily dose is 1-30 mg, which can be administrated in a single dose or multiple doses, 1-4 times a day.

The present invention provides an instant release pharmaceutical preparation, including tablet and capsule preparations, which comprises an anticoagulant drug: vicagrel or a salt, a solvate, or other pharmaceutically acceptable carriers of vicagrel.

The instant release preparation of the present invention may be a capsule or a tablet, and is embodied as drug-containing particles filled into a capsule or compressed into a tablet.

The "drug-containing particles" described herein include, but are not limited to, particles prepared by mixing particles obtained through internally adding adjuvant with externally added adjuvant by means of high shear granulation, roller compaction, spray drying granulation, layering granulation, etc., and also include mixed powders formed by directly mixing the active pharmaceutical ingredient (API) with appropriately selected excipients.

The instant release preparation of the present invention may comprise the pharmaceutical excipients indicated herein, to aid in forming particles, particulates, or powders for filling capsules or tableting.

The proportions in the drug-containing particles of the present invention are equivalent in metrics to the weight percentages of the materials before tableting or capsule filling without adding any stabilizer (optional).

In the drug-containing particles of the present invention, the proportion of the vicagrel or the pharmaceutically acceptable form thereof is 0.5%-30% wt, preferably 1%-20% wt based on the drug-containing particles.

The fillers in the drug-containing articles are present in the range of 1%-95% wt, more preferably 10%-85% wt based on the drug-containing articles. The fillers include, but are not limited to, microcrystalline cellulose, lactose, starch, pregelatinized starch, mannitol, sorbitol, and fillers known to be commonly used in the art. Microcrystalline cellulose, lactose, pregelatinized starch and mannitol are preferred, wherein lactose is present in the range of 10%-75% wt of the drug-containing particles, mannitol is present in the range of 10%-75% wt of the drug-containing particles, pregelatinized starch is present in the range of 5%-65% wt of the drug-containing particles, and microcrystalline cellulose is present in the range of 10% to 60% wt of the drug-containing particles.

The binders are present in an amount ranging from 0%-20% wt, preferably 1%-10% wt based on the drug-containing particles. Suitable binders include, but are not limited to, hydroxypropyl methylcellulose, hydroxypropyl cellulose, polyvinylpyrrolidone, ethyl cellulose, or other conventional binders, or a mixture thereof. Hydroxypropyl methylcellulose and hydroxypropyl cellulose are preferred.

The disintegrants are present in an amount ranging from 0%-20% wt, preferably 1%-10% wt based on the drug-containing particles. Suitable disintegrants include, but are not limited to, low-substituted hydroxypropyl cellulose, sodium carboxymethyl starch, croscarmellose sodium, and crospovidone. Sodium carboxymethyl starch and low-substituted hydroxypropyl cellulose are preferred.

The glidants/lubricants are present in an amount ranging from 0%-5% wt, preferably 0.2%-2% wt based on the drug-containing particles. Suitable glidants/lubricants include hydrogenated vegetable oils, silicon dioxide, magnesium stearate, sodium stearyl fumarate, preferably stearic acid and sodium stearyl fumarate.

According to the present invention, a preferred formulation of the drug-containing particles is as follows:

| Raw material | Possible application range (wt % based on drug-containing particles) | Preferred range |
| --- | --- | --- |
| vicagrel | 0.5-30% | 1-20% |
| filler | 1-95% | 10-85% |
| lactose | 0-95% | 10-75% |
| microcrystalline cellulose | 0-95% | 10-60% |
| pregaletinized starch | 0-95% | 5-65% |
| mannitol | 0-95% | 10-75% |
| binder | 0-20% | 1-10% |
| hydroxypropyl methylcellulose | 0-20% | 1-10% |
| hydroxypropyl cellulose | 0-20% | 1-10% |
| disintegrant | 0-20% | 1-10% |
| sodium carboxymethyl starch | 0-20% | 1-10% |
| low-substituted hydroxypropyl cellulose | 0-20% | 1-10% |
| lubricant/glidant | 0-5% | 0.2-2% |
| magnesium stearate | 0-5% | 0.2-2% |
| sodium stearyl fumarate | 0-5% | 0.2-2% |

The present invention further provides a method for preparing the instant release preparation, which comprises the following steps:

a) providing micronized active ingredient powders of vicagrel, D90<50 μm, wherein the active ingredient powder of vicagrel refers to a micronized form of vicagrel or a pharmaceutically acceptable form thereof;

b) mixing the vicagrel active ingredient powders with additives to make drug-containing particles; and c) subjecting the drug-containing particles to filling, tableting or filling, to obtain vicagrel capsules or tablets.

In step a) of the present method, the pulverization method of micronization is performed by conventional pulverization techniques in the art, including, but not limited to, grinding, extrusion, collision, and shearing, and the pulverization device used includes, but is not limited to, a ball mill, a jet mill and a hammer mill. More preferably, a jet mill device is used.

In step b) of the present method, the preparation of the drug-containing granules can be carried out by means of dry granulation, wet granulation or direct mixing, specifically:

b1) An active ingredient of vcagrel is mixed together with one or more fillers in any desired order; in other embodiments, vicagrel or a pharmaceutically acceptable carrier thereof may be mixed together with one or more fillers and optionally one or more of the following compounds in any desired order: one or more binders; one or more disintegrants; and one or more glidants/lubricants; the mixing method uses a conventional mixing apparatus in the art including, but not limited to, a three-dimensional mixer, a V-type mixer, or a device with the mixing principle of stirring or fluidization.

b2) Optionally, the wet or dry method is used for granulation. With the wet granulation method, the mixed materials in b1) are aggregated to form particles by a wet granulation apparatus after spraying a binder, and then the particles are dried and sized; and with the dry granulation method, the mixed materials in b1) are rolled by a dry granulator after adding a lubricant to form a material strip, and the strip is pulverized and sieved to obtain particles. The wet granulation method includes conventional methods such as high-shear mixing granulation, fluidized bed granulation, non-perforated pan layering granulation and the like. The dry granulation means that the material is pre-compacted, and then rolled through a horizontal or vertical roller to form a material strip, and then the strip is pulverized to form particles.

b3) Optionally, if the wet granulation method is used, the particles need to be dried, and the temperature of the material during the drying process is controlled below 60° C.; the apparatus used in the drying process includes, but is not limited to, a blast drying oven, a fluidized bed.

b4) The particles from the step b1), b2) or b3) are mixed with glidants/lubricants, and/or disintegrants and fillers that need to be added, to obtain drug-containing particles.

In step c) of the present method, one or more stabilizers may be also added in the drug-containing particles for filling, tableting or filling; the weight ratio of the stabilizers to the drug-containing particles is 0-5:100, preferably 0.2-1:100.

The stabilizer is selected from fumaric acid, citric acid, citric acid, hydrogenated castor oil, hydrogenated soybean oil, glyceryl behenate, methyl silicone oil, and dimethyl silicone oil.

Still further, for the tablet obtained in c), a coating step may be taken to obtain a coated vicagrel tablet, and a coating component does not contain polyethylene glycol and talc. A film-forming component of a coating solution may be hydroxypropyl methylcellulose, hydroxypropyl cellulose or polyvinyl alcohol. A lake may be added to adjust the color, and includes iron oxide, titanium dioxide and other common lakes/pigments for coating in the art. Commercially available coating formulations often contain a plasticizer polyethylene glycol and an anti-sticking agent talc, while the present invention does not contain polyethylene glycol and talc.

With regard to the drug-containing particles obtained according to the present invention, a pharmaceutical preparation formed therefrom exhibits rapid release characteristics in an in vitro dissolution test and exhibits considerable advantages in pharmacokinetics in vivo, showing a greater degree (area under the curve (AUC)) and rate (maximum concentration ($C_{max}$)) of drug absorption.

According to the formulation and preparation method of the drug-containing particles provided by the present invention, an instant release preparation with high in vivo bioavailability and blood drug concentration can be provided, and according to the formulation of the drug-containing particles provided by the present invention, a capsule or tablet instant release preparation having excellent stability can be obtained by means of a combination of optional preparation steps.

DETAILED DESCRIPTION OF THE INVENTION

Figure 1:
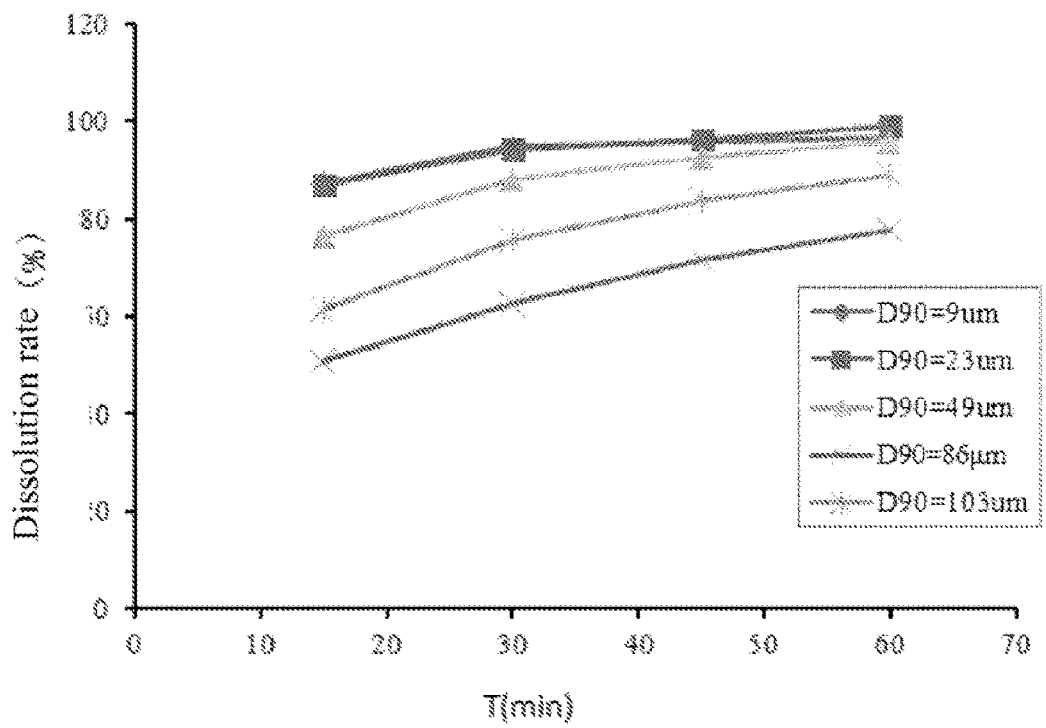
FIG. 1 is a dissolution curve of a vicagrel preparation at different particle sizes.

The Detailed Description is given below. It should be understood that the present invention is not limited to these specific embodiments. Those skilled in the art can make various modifications and changes to the present invention without departing from the spirit and scope of the present invention. Such improvements are considered to be included within the scope of the claims appended to this application. Examples are a further description of the contents of the present invention to illustrate the innovation of the present invention.

Example 1 Vicagrel Capsule

| Raw material | Amount mg/capsule |
| --- | --- |
| vicagrel | 20 |
| pregaletinized starch | 100 |
| microcrystalline cellulose | 79.5 |
| glyceryl behenate | 0.5 |
| total | 200 |

Vicagrel was pulverized by a hammer mill (Frewitt) with a 0.20 mm sieve, at 6000 rpm, and a 1 kg/min feed rate, and it was determined that D90=43 μm. The pulverized vicagrel was mixed with microcrystalline cellulose and lactose in a three-dimensional mixer for 15 min, hydrogenated castor oil was added and mixed, and the resulting particles were filled in size 3 capsules.

Example 2 Vicagrel Capsule

| Raw material | Amount mg/capsule |
| --- | --- |
| vicagrel | 5.5 |
| microcrystalline cellulose | 100 |
| lactose | 80 |
| sodium carboxymethyl starch | 20 |
| hydroxypropyl methylcellulose | 6.5 |
| water | q.s |
| magnesium stearate | 0.5 |
| total | 212.5 |

The raw materials were pulverized using a QL-100 jet mill at a pressure 0.8 MPa, a working temperature of 15° C., and a pulverization time of 10 min, and it was determined that D90=9 μm. The pulverized vicagrel hydrochloride was mixed with microcrystalline cellulose, lactose, sodium carboxymethyl starch, and hydroxyl propyl methylcellulose in a three-dimensional mixer at 35 rpm for 10 min, the mixture was removed and placed in a high-shear wet granulator, stirred at 500 rpm, and granulated at a shearing rate of 1,000 rpm with added water. Particles were then sized by passing through a 16-mesh sieve, and dried in an air dry oven at 60° C., removed, and sized by passing through a 24-mesh sieve, and magnesium stearate was added and mixed. The drug-containing granules were filled in size 3 capsules to obtain vikagrel instant release capsules.

Example 3 Vicagrel Capsule

| Raw material | Amount mg/capsule |
| --- | --- |
| vicagrel | 15 |
| pregaletinized starch | 49.5 |
| lactose | 140 |
| sodium carboxymethyl starch | 20 |
| hydroxypropyl methylcellulose | 5 |
| water | q.s |
| sodium stearyl fumarate | 0.5 |
| total | 230 |

The pulverized vicagrel salt was placed with pregelatinized starch, lactose, and sodium carboxymethyl starch in a fluidized bed, fluidized mixing is started for 10 min, and 5% hydroxypropyl methylcellulose is prepared as a binder. At an air inlet temperature of 80° C., the binder was sprayed while maintaining a bed temperature at 40-50° C. The formed particles were dried for 30 min while the bed temperature was maintained at 50-60° C., and were discharged. Sodium stearyl fumarate was added and mixed for 5 min, and the particles were filled into capsules.

Example 4

Vicagrel was pulverized into powders with different particle sizes, and drug-containing particles were prepared and filled in capsules. The dissolution rate was measured at 50 rpm using a pH 4.0 acetate buffer containing 0.2% SDS as a medium, according to the USPII method. The results are shown in the following table and FIG. 1.

In treatments 1, 2, and 3, when the particle size of API was below 50 μm, the release rate at 30 min of >85% could be satisfied. In particular, when the particle size was <30 μm, the release rate at 15 min was >85%. In treatment 4 and treatment 5, the particle size of API was >50 μm, and the in vitro release rate was slow, and the dissolution rate at 45 min was less than 85%.

| Time (min) | Treatment 1 D90 = 9 um | Treatment 2 D90 = 23 um | Treatment 3 D90 = 49 um | Treatment 4 D90 = 86 μm | Treatment 5 D90 = 103 um |
|---|---|---|---|---|---|
| 15 | 87.36 | 86.98 | 76.36 | 50.9 | 61.51 |
| 30 | 94.85 | 94.35 | 88.07 | 62.6 | 75.64 |
| 45 | 95.88 | 96.28 | 92.57 | 71.6 | 83.67 |
| 60 | 96.67 | 98.91 | 95.95 | 77.8 | 88.83 |
| 90 | / | 100.59 | 97.62 | 94.9 | 93.06 |
| 120 | / | / | 99.69 | / | 96.09 |
| 180 | / | / | 100.11 | / | 98.92 |

Following the method in Example 2, vicagrel capsules were prepared with the raw materials of different particle sizes, and the blood drug concentration and pharmacokinetic parameters of active metabolites were measured after administration to Beagle dogs, specifically as follows:

8 healthy beagle dogs, male, age 7-8 months, weight 8-10 kg, cross-over. The dogs were fasted for 12 h before the test and provided with food 4 h after the administration, and water was not forbidden throughout the test. The wash-out period between cycles was 7 days. The administration was done with 40 ml water. 1 ml of venous blood was taken from limb veins at the following set time points: before administration (0 h) and 10 min, 20 min, 40 min, 1.0 h, 1.5 h, 2.0 h, 4.0 h, 6.0 h, 8.0 h, 12 h and 24 h after administration, and the samples were processed according to relevant standard operating procedures, and then cryopreserved in a refrigerator at −70° C. for test. The concentrations of a metabolite M9-2 and active metabolites M15-1 and M15-2 of vicagrel in plasma were determined using LC-MS/MS method. The main pharmacokinetic parameters of a metabolite M9-2 and active metabolites M15-1 and M15-2 of vicagrel after administration to beagle dogs were calculated using a non-compartmental approach with PhoenixWinNonlin6.4 software. The results are shown in the table below (n=8).

| Main metabolite | PK parameter | Particle size (μm) | | | |
|---|---|---|---|---|---|
| | | 9 | 23 | 49 | 86 |
| active metabolite M9-2 | $C_{max}$(ng/mL) | 95.4✻ | 60.5 * | 62.3 * | 46.7 |
| | $AUC_{0-t}$(ng · h/mL) | 244 | 242 * | 249 * | 190 |
| active metabolite M15-1 | $C_{max}$(ng/mL) | 195.8✻ | 87.9 | 90.1 | 80.0 |
| | $AUC_{0-t}$(ng · h/mL) | 121.6✻ | 83.9 | 88.6 | 86.7 |
| active metabolite M15-2 | $C_{max}$(ng/mL) | 76.4✻ | 40.1 | 40.3 | 32.3 |
| | $AUC_{0-t}$(ng · h/mL) | 53.6✻ | 37.3 | 38.3 | 33.8 |

✻ indicates P < 0.05 compared with a particle size group of 23, 49, or 86 μm.
* indicates P < 0.05 compared with a particle size group of 86 μm.

The structural formula of M9-2 is:

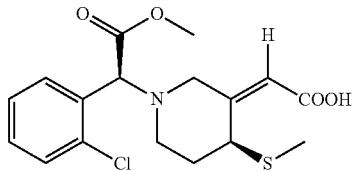 [SMILES: COC(=O)[C@H](c1ccccc1Cl)N1CC[C@H](SC)/C(=C\C(=O)O)C1]

The structural formula of M15-1 is:

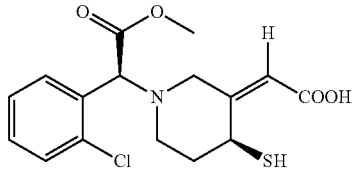 [SMILES: COC(=O)[C@H](c1ccccc1Cl)N1CC[C@H](S)/C(=C\C(=O)O)C1]

The structural formula of M15-2 is:

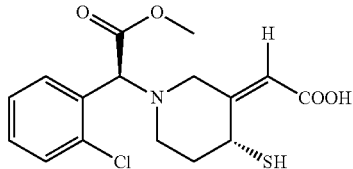 [SMILES: COC(=O)[C@H](c1ccccc1Cl)N1CC[C@@H](S)/C(=C\C(=O)O)C1]

Figure 2:
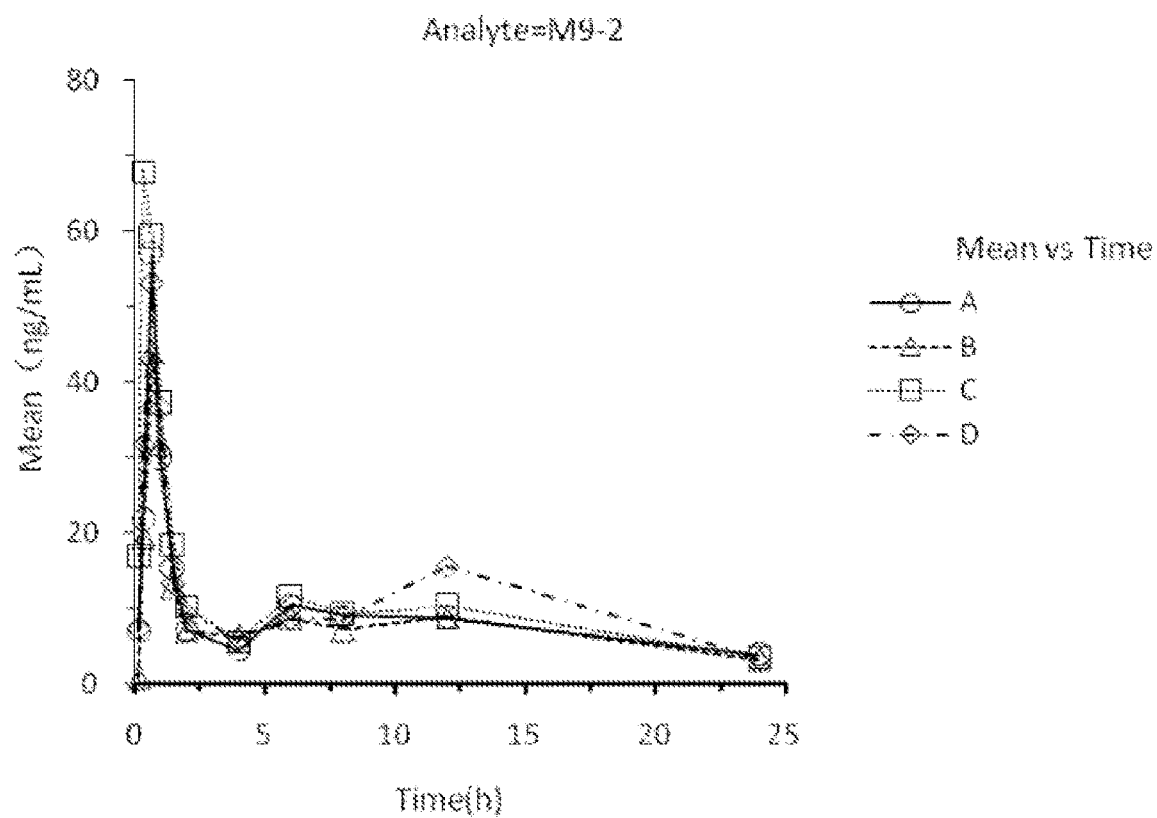
FIG. 2 is a blood drug concentration curve of M9-2 in dogs after administration of a vicagrel preparation prepared with different particle sizes. A: D90=23 μm; B: D90=86 μm; C: D90=9 μm; and D: D90=49 μm.
Figure 3:
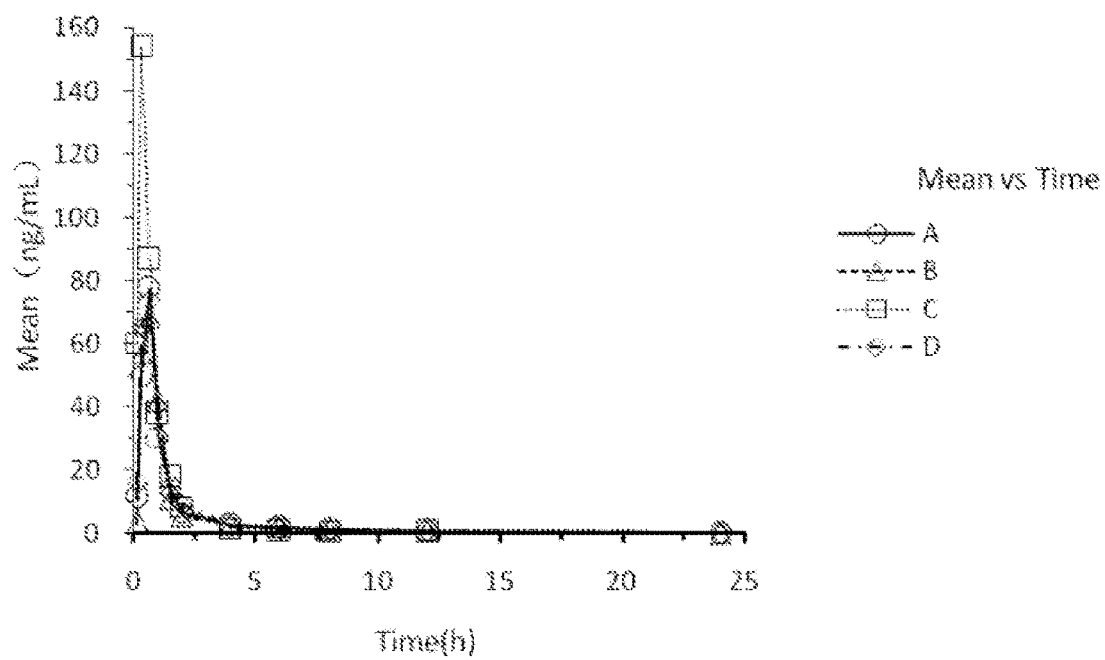
FIG. 3 is a blood drug concentration curve of M15-1 in dogs after administration of a vicagrel preparation prepared with different particle sizes. A: D90=23 μm; B: D90=86 μm; C: D90=9 μm; and D: D90=49 μm.
Figure 4:
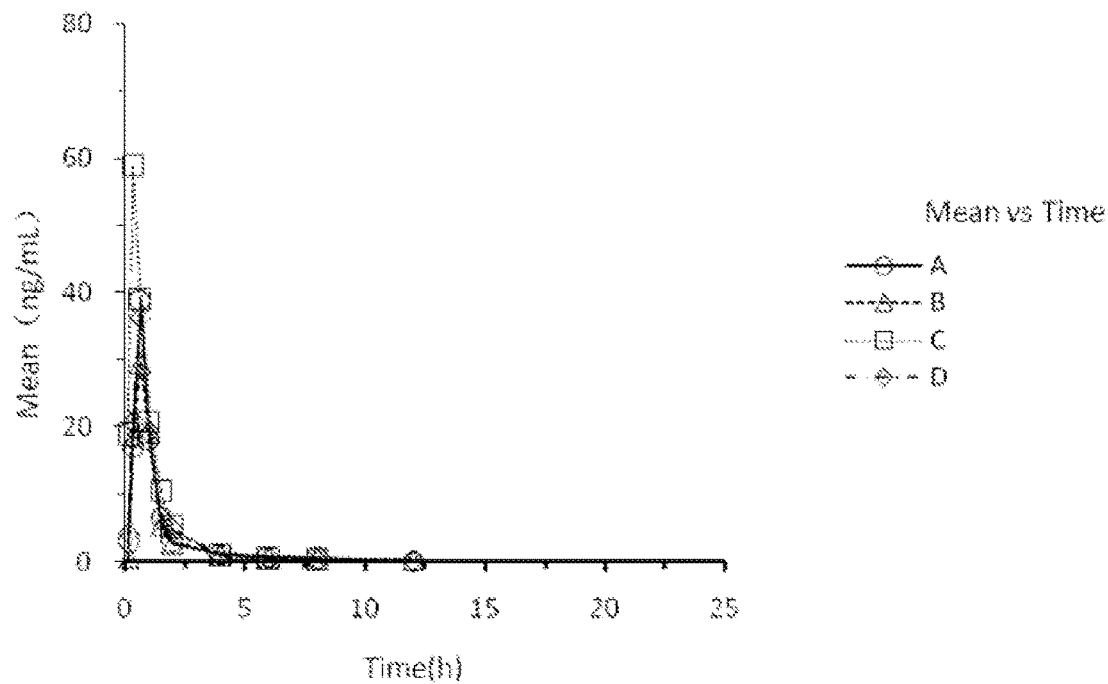
FIG. 4 is a blood drug concentration curve of M15-2 in dogs after administration of a vicagrel preparation prepared with different particle sizes. A: D90=23 μm; B: D90=86 μm; C: D90=9 μm; and D: D90=49 μm.

Blood drug concentration curves of M9-2, M15-1 and M15-2 in dogs after administration of a vicagrel preparation prepared with different particle sizes are shown in FIG. 2, FIG. 3 and FIG. 4, respectively.

When the particle size of the raw material is less than 50 μm, it can be seen that the AUC of the drug is significantly higher than that of the particle size group of 86 μm. In particular, when the particle size of the drug is less than 15

μm, it is observed that the area under blood drug concentration-time curve of active metabolites A, B, and C, and the $C_{max}$ of active metabolites B and C are significantly higher than those of other groups with a particle size >15 μm. This is very beneficial for the anticoagulant drugs to exert their effects.

Example 5 Vicagrel Tablet

| Raw material | Amount mg/tablet |
| --- | --- |
| vicagrel | 5 |
| pregaletinized starch | 57.5 |
| mannitol | 22.5 |
| low-substituted hydroxypropyl cellulose | 10 |
| hydroxypropyl methylcellulose | 4 |
| water | q.s |
| sodium stearyl fumarate | 1 |
| total | 200 |

The pulverized vicagrel was subjected to stirred mixing with pregaletinized starch, mannitol, low-substituted hydroxypropyl cellulose, and hydroxypropyl methyl cellulose in a high-shear granulator for 5 min, stirred at a linear speed of 4 m/s, and sheared with a shearer at 800 rpm, and granulated with added water, the particles were deagglomerated through a 10-mesh sieve, and dried in a fluidized bed while maintaining the bed temperature below 60° C. during drying. The particles were removed, and sized through a 24-mesh sieve, and sodium stearyl fumarate was added and mixed, and tableting was performed on a 10-punch rotary tablet press (ZP-10A, Sinopharm Longli), with a 8 mm shallow concave punch.

Example 6 Vicagrel Tablet

| Raw material | Amount mg/tablet |
| --- | --- |
| vicagrel | 10 |
| pregaletinized starch | 40 |
| microcrystalline cellulose | 102 |
| croscarmellose sodium | 20 |
| polyvinylpyrrolidone | 7 |
| water | q.s |
| magnesium stearate | 1 |
| total | 180 |

The pulverized vicagrel was mixed with pregaletinized starch, microcrystalline cellulose, polyvinylpyrrolidone, and half of the amount of croscarmellose sodium and half of the amount of magnesium stearate in a V-type mixer for 10 min. The material was put into a dry granulator (LGJ-300) where granulation was operated at parameters of a feed rate of 20 Hz, roller speed of 15 rpm, extrusion force of 6 bar, screen of 20 mesh, and shearing speed of 300 rpm. The particles were mixed with the rest of the disintegration and the lubricant for 5 min to obtain drug-containing particles, which were subjected to further tableting operation.

Example 7 Vicagrel Tablet

| Raw material | Amount mg/tablet |
| --- | --- |
| vicagrel | 10 |
| pregaletinized starch | 35 |
| lactose | 108 |
| low-substituted hydroxypropyl cellulose | 11 |
| hydroxypropyl methylcellulose | 4 |
| water | q.s |
| sodium stearyl fumarate | 1 |
| glyceryl behenate | 1 |
| total | 170 |

The pulverized vicagrel was subjected to stirred mixing with pregaletinized starch, lactose, low-substituted hydroxypropyl cellulose, and hydroxypropyl methyl cellulose in a wet granulator, and granulated with added water. The particles were sized through a 16-mesh sieve and dried in an air dry oven at 55° C., removed, and ground and sized through a conical mill. Sodium stearyl fumarate was added and mixed for 3 min, and the stabilizer glyceryl behenate was added and mixed for 3 min. The particles were removed, and tableted with a 7.5 mm shallow concave punch, having a hardness >6 kgf.

Example 8 Vicagrel Tablet

| Raw material | Amount mg/tablet |
| --- | --- |
| vicagrel | 10 |
| pregaletinized starch | 42 |
| mannitol | 106 |
| low-substituted hydroxypropyl cellulose | 12 |
| hydroxypropyl methylcellulose | 8 |
| water | q.s |
| sodium stearyl fumarate | 1 |
| fumaric acid | 1 |
| total | 170 |

The pulverized vicagrel was subjected to stirred mixing with pregaletinized starch, mannitol, low-substituted hydroxypropyl cellulose, and hydroxypropyl methyl cellulose in a wet granulator, and granulated with added water. The particles were sized through a 16-mesh sieve and dried in an air dry oven at 55° C., removed, and ground and sized through a conical mill. Sodium stearyl fumarate was added and mixed for 3 min, and the stabilizer glyceryl behenate was added and mixed for 3 min. The particles were removed, and tableted with a 7.5 mm shallow concave punch, having a hardness >6 kgf.

Example 9 Coated Vicagrel Tablet

The tablet core prepared in Example 8 was coated with a BG-10 type coating machine using Opadry II coating powder, with the coating powder being free of polyethylene glycol and talc. The tablet core was 600 g, the air inlet temperature was 50° C., the coating flow rate was 4 g/min, the air inlet volume was 60 m³/h, and the bed temperature was 35-45° C. Vicagrel coating tablets were obtained.

Example 10 Effect Comparison of Stabilizers

Vicagrel tablets were prepared following Example 7 and Example 8, except that no stabilizers were added after drug-containing particles were obtained. The resulting tablets were sealed in HDPE bottles and placed at 60° C. for 10 days, and the related substances and the dissolution were determined.

| | Maximum single impurity and total impurity after placing in 60° C. HDPE bottles for 10 days | | | |
|---|---|---|---|---|
| Impurity | Example 7 | Example 7 (without stabilizer) | Example 8 | Example 8 (without stabilizer) |
| maximum single impurity | 0.88 | 2.04 | 0.79 | 1.76 |
| total impurity | 1.09 | 2.78 | 0.97 | 2.21 |
| dissolution 0 day | 95.1% | 94.6% | 92.8% | 93.1% |
| (45 min) 10 days | 94.3% | 83% | 93% | 85% |

It can be seen that, when the drug-containing particles are mixed with the stabilizer and tableted, the increase in related substances is reduced, and the dissolution is not significantly reduced.

Example 11 Stability Comparison of Coated Tablets

Vicagrel tablet was prepared following Example 8, and coated in accordance with the parameters in Example 9, except that the coating solution contains a common plasticizer polyethylene glycol and anti-sticking agent talc.

| | Maximum single impurity and total impurity after placing in 60° C. HDPE bottles for 10 days | | | |
|---|---|---|---|---|
| Impurity | Example 9 (without polyethylene glycol and talc in coating powder) | Example 9 (with polyethylene glycol and talc in coating powder) | Example 9 (with polyethylene glycol in coating powder) | Example 9 (with talc in coating powder) |
| maximum single impurity | 0.88 | 3.04 | 1.89 | 2.69 |
| total impurity | 1.11 | 4.06 | 2.62 | 3.67 |
| dissolution 0 day | 94.6% | 95.1% | 96.9% | 93.0% |
| (45 min) 10 days | 93.8% | 81.4% | 85.8% | 87.3% |

It is surprisingly found that when the coating component does not contain polyethylene glycol and talc, the vicagrel tablet can still provide a good coating membrane and is easy to prepare, and its stability is significantly increased compared to coated tablets with the above ingredients added.

What is claimed is:

1. An instant release pharmaceutical preparation, wherein the preparation is a tablet or a capsule, and comprises the following components:
   a) a vicagrel compound, or a pharmaceutically acceptable salt thereof in the range 0.5%-30% wt of the tablet or capsule filling;
   b) one or more fillers in the range of 1%-95% wt of the tablet or capsule filling, wherein the filler is selected from microcrystalline cellulose, lactose, starch, pregelatinized starch, mannitol or sorbitol;
   c) one or more binders in the range of 0%-20% wt of the tablet or capsule filling, wherein the binder is selected from hydroxypropyl methyl cellulose, hydroxypropyl cellulose, polyvinylpyrrolidone or ethyl cellulose;
   d) one or more disintegrants in the range of 0%-20% wt of the tablet or capsule filling, wherein the disintegrant is selected from low-substituted hydroxypropyl cellulose, sodium carboxymethyl starch, croscarmellose sodium, or crospovidone; and
   e) one or more glidants/lubricants in the range of 0%-5% wt of the tablet or capsule filling, wherein the glidant/lubricant is selected from hydrogenated vegetable oil, silicon dioxide, magnesium stearate or sodium stearyl fumarate;

wherein the vicagrel compound or the pharmaceutically acceptable salt thereof is provided in form of particles, wherein 90% of said particles have a diameter (D90) of less than 50 μm.

2. The preparation according to claim 1, wherein the preparation consists of the following components:
   a) the vicagrel compound or a pharmaceutically acceptable salt thereof in the range of 0.5%-30% wt of the tablet or capsule filling;
   b) the fillers in the range of 1%-95% wt of the tablet or capsule filling;
   c) the binders in the range of 0%-20% wt of the tablet or capsule filling;
   d) the disintegrants in the range of 0%-20% wt of the tablet or capsule filling; and
   e) the glidants/lubricants in the range of 0%-5% wt of the tablet or capsule filling;
   wherein the sum of the percentages of all components being 100%.

3. The preparation according to claim 1, wherein the D90 is less than 30 μm.

4. The preparation according to claim 3, wherein the D90 is less than 15 μm.

5. A method for preparing the instant release pharmaceutical preparation according to claim 1, comprising the following steps:
   a) providing micronized active ingredient powders of vicagrel with a D90 less than 50 μm, wherein the active ingredient powder of vicagrel refers to a micronized form of vicagrel compounds or a pharmaceutically acceptable salt thereof;
b) mixing the vicagrel active ingredient powders with (i) one or more fillers; (ii) one or more binders; (iii) one or more disintegrants; (iv) one or more glidants/lubricants to make drug containing particles; and
c) filling and tableting the drug-containing particles to obtain vicagrel capsules or tablets.

6. The preparation method according to claim 5, wherein for the tablet obtained in c), a coating step is further taken to obtain a coated vicagrel tablet, and a coating component does not contain polyethylene glycol and talc.

\* \* \* \* \*